US008932607B2

(12) United States Patent  
Custers et al.

(10) Patent No.: US 8,932,607 B2  
(45) Date of Patent: Jan. 13, 2015

(54) BATCHES OF RECOMBINANT ADENOVIRUS WITH ALTERED TERMINAL ENDS

(71) Applicant: Crucell Holland B.V., Leiden (NL)

(72) Inventors: Jerome H. H. V. Custers, Alphen aan den Rijn (NL); Jort Vellinga, Leiden (NL)

(73) Assignee: Crucell Holland B.V., Leiden (NL)

( * ) Notice: Subject to any disclaimer, the term of this patent is extended or adjusted under 35 U.S.C. 154(b) by 45 days.

(21) Appl. No.: 13/794,318

(22) Filed: Mar. 11, 2013

(65) Prior Publication Data

US 2014/0073032 A1   Mar. 13, 2014

Related U.S. Application Data

(60) Provisional application No. 61/609,678, filed on Mar. 12, 2012.

(51) Int. Cl.
| | |
|---|---|
| *A61K 39/23* | (2006.01) |
| *A61K 39/12* | (2006.01) |
| *C12N 7/02* | (2006.01) |
| *C12N 7/00* | (2006.01) |

(52) U.S. Cl.
CPC ........ *C12N 7/00* (2013.01); *C12N 2760/16234* (2013.01); *C12N 2760/16121* (2013.01); *C12N 2750/14143* (2013.01); *C12N 2760/16151* (2013.01); *C12N 2710/10321* (2013.01); *C12N 2710/10343* (2013.01)
USPC ................ 424/233.1; 424/204.1; 424/205.1; 435/239

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 5,122,458 | A | 6/1992 | Post et al. |
| 5,385,839 | A | 1/1995 | Stinski |
| 5,559,099 | A | 9/1996 | Wickham et al. |
| 5,837,511 | A | 11/1998 | Falck-Pedersen et al. |
| 5,837,520 | A | 11/1998 | Shabram et al. |
| 5,846,782 | A | 12/1998 | Wickham et al. |
| 5,851,806 | A | 12/1998 | Kovesdi et al. |
| 5,891,690 | A | 4/1999 | Massie |

(Continued)

FOREIGN PATENT DOCUMENTS

| | | |
|---|---|---|
| WO | 9003184 | 4/1990 |
| WO | 9014837 | 12/1990 |

(Continued)

OTHER PUBLICATIONS

GenBank JN860679.1; Dehghan, et al. 2011.*

(Continued)

*Primary Examiner* — Zachariah Lucas  
*Assistant Examiner* — Stuart W Snyder  
(74) *Attorney, Agent, or Firm* — TraskBritt, P.C.

(57) ABSTRACT

Described is a composition comprising a plurality of recombinant adenovirus particles, being a recombinant human adenovirus of serotype 5, 26, 34, 35, 48, 49 or 50, or a recombinant simian adenovirus, characterized in that the genomes of essentially all adenovirus particles in the composition comprise as the 5' terminal nucleotides the nucleotide sequence: CTATCTAT (nucleotides 1-8 of SEQ ID NO:7). Also described are methods to produce such compositions.

46 Claims, 3 Drawing Sheets

(56) References Cited

U.S. PATENT DOCUMENTS

| | | | |
|---|---|---|---|
| 5,965,541 | A | 10/1999 | Wickham et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 6,020,191 | A | 2/2000 | Scaria et al. |
| 6,040,174 | A | 3/2000 | Imler et al. |
| 6,083,716 | A | 7/2000 | Wilson et al. |
| 6,113,913 | A | 9/2000 | Brough et al. |
| 6,225,289 | B1 | 5/2001 | Koveski et al. |
| 6,261,823 | B1 | 7/2001 | Tang et al. |
| 7,270,811 | B2 | 9/2007 | Bout et al. |
| 7,326,555 | B2 | 2/2008 | Konz, Jr. et al. |
| 2005/0265973 | A1 | 12/2005 | Harden et al. |
| 2009/0227000 | A1 | 9/2009 | Harden et al. |
| 2010/0136658 | A1 | 6/2010 | Hermiston et al. |
| 2012/0231524 | A1 | 9/2012 | Harden et al. |

FOREIGN PATENT DOCUMENTS

| | | | |
|---|---|---|---|
| WO | 9611711 | | 4/1996 |
| WO | 9802522 | | 1/1998 |
| WO | 9822588 | | 5/1998 |
| WO | 9839411 | | 9/1998 |
| WO | 9912568 | | 3/1999 |
| WO | 9941416 | | 8/1999 |
| WO | 9955132 | | 11/1999 |
| WO | 0029024 | | 5/2000 |
| WO | 0032754 | | 6/2000 |
| WO | 0070071 | | 11/2000 |
| WO | 0102607 | | 1/2001 |
| WO | 0136615 | | 3/2001 |
| WO | 0134940 | | 5/2001 |
| WO | 0166137 | | 9/2001 |
| WO | 0222080 | | 3/2002 |
| WO | 0240665 | | 5/2002 |
| WO | 03049763 | | 6/2003 |
| WO | 03061708 | | 7/2003 |
| WO | 03078592 | | 9/2003 |
| WO | 03104467 | | 12/2003 |
| WO | 2004001032 | | 12/2003 |
| WO | 2004004762 | | 1/2004 |
| WO | 2004020971 | | 3/2004 |
| WO | 2004037294 | | 5/2004 |
| WO | 2004055187 | | 7/2004 |
| WO | 2005002620 | | 1/2005 |
| WO | 2005071093 | | 8/2005 |
| WO | 2005080556 | | 9/2005 |
| WO | 2005118825 | A2 | 12/2005 |
| WO | 2006008468 | | 1/2006 |
| WO | 2006053871 | | 5/2006 |
| WO | 2006108707 | | 10/2006 |
| WO | 2006120034 | | 11/2006 |
| WO | 2007104792 | | 9/2007 |
| WO | 2007110409 | | 10/2007 |
| WO | 2008080003 | | 7/2008 |
| WO | 2009026183 | | 2/2009 |
| WO | 2009117134 | | 9/2009 |
| WO | 2010060719 | | 6/2010 |
| WO | 2010085984 | | 8/2010 |
| WO | 2010086189 | | 8/2010 |
| WO | 2010096561 | | 8/2010 |
| WO | 2011045378 | | 4/2011 |
| WO | 2011045381 | | 4/2011 |
| WO | 2011098592 | | 8/2011 |

OTHER PUBLICATIONS

Abbink et al.; Comparative Seroprevalence and Immunogenicity of Six Rare Serotype Recombinant Adenovirus Vaccine Vectors from Subgroups B and D; Journal of Virology; vol. 81, No. 9; May 2007; p. 4654-4663.
Abrahamsen et al.; Construction of an adenovirus type 7a E1A-vector; Journal of Virology; vol. 71, No. 11; Nov. 1997; p. 8946-8951.
Alestrom et al.; A common sequence in the inverted terminal repetitions of human and avian adenoviruses; Gene, 18 (1982) 193-197.
Bangari et al.; Development of nonhuman adenoviruses as vaccine vectors; Vaccine, Feb. 13, 2006; 24(7): 849-862.
Bernstein et al.; Template Requirements for in Vivo Replication of Adenovirus DNA; Molecular and Cellular Biology, Jun. 1986, p. 2115-2124.
Brough et al.; A Gene Transfer Vector-Cell Line System for Complete Funtional Complementation of Adenovirus Early Regions E1 and E4; Journal of Virology, Sep. 1996, p. 6497-6501.
Challberg et al.; Template requirements for the initiation of adenovirus DNA replication; Proc. Natl. Acad. Sci; vol. 81, pp. 100-104, Jan. 1984.
Cohen et al.; Chimpanzee adenovirus CV-68 adapted as a gene delivery vector interacts with the coxsackievirus and adenovirus receptor; Journal of General Virology (2002), 83, 151-155.
Dan et al.; Four New Inverted Terminal Repeat Sequences from Bovine Adenoviruses Reveal Striking Differences in the Length and Content of the ITRs; Virus Gene 22:2, 175-179, 2001.
De Jong et al.; Adenovirus DNA Replication: Protein Priming, Jumping Back and the Role of the DNA Binding Protein DBP; Curr Top Microbiol Immunol 272: 187-211.
European Search Report; EP 12 15 9009; dated Apr. 12, 2012.
Fallaux et al.; New Helper Cells and Matched Early Region 1-Deleted Adenoviurs Vectors Prevent Generation of Replication-Competent Adenoviruses; Human Gene Therapy 9:1909-1919 (Sep. 1, 1998).
Farina et al.; Replication-Defective Vector Based on a Chimpanzee Adenovirus; Journal of Virology, vol. 75, No. 23; Dec. 2001, p. 11603-11613.
Gao et al.; A Cell Line for High-Yield Production of E1-Deleted Adenovirus Vectors without the Emergence of Replication-Competent Virus; Human Gene Therapy 11:213-219 (Jan. 1, 2000).
Geisbert et al.; REcombinant Adenvorus Serotype 26 (Ad26) and Ad35 Vaccine Vectors Bypass Immunity to Ad5 and Protect Nonhuman Primates against Ebolavirus Challenge; Journal of Virology, May 2011, p. 4222-4233.
Goerke et al.; Development of a Novel Adenvorus Purification Process Utilizing Selective Precipitation of Cellular DNA; Biologics Development & Enginerring, BioProcess R&D, Merck Research Laboratories, Published online May 11, 2005; 10 pages.
Guggenheimer et al.; DNA sequences required for the in vitro replication of adenovirus DNA; Proc. Natl. Acad. Sci; vol. 81, pp. 3069-3073; May 1984.
Harris, Mark P.G.; DNA Sequences Required for the Initiation of Adenovirus Type 4 DNA Replication in Vitro; J. Mol. Biol. (1988) 201, 57-67.
Havenga et al.; Improved Adenovirus Vectors for Infection of Cardiovascular Tissues; Journal of Virology; vol. 75, No. 7; Apr. 2001; p. 3335-3342.
Havenga et al.; Novel replication-incompetent adenoviral B-group vectors: high vector stability and yield in PER.C6 cells; Journal of General Virology (2006), 87, 2135-2143.
Hay, Ronald T.; The origin of adenovirus DNA replication: minimal DNA sequence requirement in vivo; The EMBO Journal vol. 4, No. 2; pp. 421-426; 1985.
Hoganson et al.; Development of a Stable Adenoviral Vector Formulation; Bioprocessing Mar. 2002, p. 43-48.
Horwitz, Marshall S.; Adenoviruses; Fields Virology, Third Edition; Chapter 68, 1996; 23 pages.
Houng et al.; Emergence of a new human adenovirus type 4(Ad4) genotype: Identification of a novel inverted terminal repeated (ITR) sequence from majority of Ad4 isolates from US military recruits; Journal of Clinical Virology 35 (2006) 381-387.
Hu et al.; Comparative immunogenicity of recombinant adenovirus-vectored vaccines expressing different forms of hemagglutinin (HA) proteins from the H5 serotype of influencza A viruses in mice; Virus Research 155 (2011) 156-162.
Jacobs et al.; Characterization and manipulation of the human adenovirus 4 genome; Journal General Virology (2004), 85, 3361-3366.

(56) References Cited

OTHER PUBLICATIONS

Kaneko et al.; Analysis of the complete genome sequence of epidemic keratoconjunctivits-related human adenovirus type 8, 19, 37 and a novel serotype; Journal of General Virology (2009) 90; 1471-1476.
King et al.; A precursor terminal protein-trinucleotide intermediate during initiation of adenovirus DNA replication: regeneration of molecular ends in vitro by a jumping back mechasism; The EMBO Journal; vol. 13, No. 23; pp. 5786-5792; 1994.
Kobinger et al.; Chimpanzee adenovirus vaccine protects against Zaire Ebola virus; Virology 346 (2006) 394-401.
Lasaro et al.; New Insights of Adenovirus as Vaccine Vectors; Molecular Therapy vol. 17, No. 8, 1333-1339; Aug. 2009.
Liu et al.; Adenovirus DNA Replication; Curr Top Microbiol Immunol 272, Chapter 5: 131-164.
Nan et al.; Development of an Ad7 cosmid system and generation of an Ad7 E1 E3HIV mn env/rev recombinant virus; Gene Therapy (2003) 10, 326-336.
Ophorst et al.; Increased immunogenicity of recombinant Ad35-based malaria vaccine through formulation with aluminium phosphate adjuvant; Vaccine (2007); 10 pages.
Purkayastha et al.; Genomic and Bioinformatics Analyses of HAdV-4vac and HAdV-7vac, Two Human Adenovirus (HAdV) Strains That Constituted Original Prophylaxis against HAdV-Related Acute Respiratory Disease, a Reemerging Epidemic Disease; Journal of Clinical Microbiology, vol. 43, No. 7; Jul. 2005, p. 3083-3094.
Rademaker et al.; Relaxed template specificity in fowl adenovirus 1 DNA replication initiation; Journal of General Virology (2006), 87, 553-562.
Radosevic et al.; Protective Immune Responses to a Recombinant Adenovirus Type 35 Tuberculosis Vaccine in Two Mouse Strains: CD4 and CD8 T-Cell Epitope Mapping and Role of Gamma Interferon; Infection and Immunity, vol. 75, No. 8; Aug. 2007; p. 4105-4115.
Shenk, Thomas; Adenoviridae: The Viruses and Their Replication; Fields Virology, Third Edition; 1996; Chapter 67; 38 pages.
Shinagawa et al.; Comparative Sequence Analysis of the Inverted Terminal Repetition in the Genomes of Animal and Avian Adenoviruses; Virology 125, 491-492 (1983).
Shinagawa et al.; Comparative sequence analysis of the inverted terminal repetitions from different adenoviruses; Proc. Natl. Acad. Sci.; vol. 77, No. 7, pp. 3831-3835, Jul. 1980.
Shinagawa et al.; Phylogenetic relationships between adenoviruses as inferred from nucleotide sequences of inverted terminal repeats; Gene, 55 (1987) 85-93.
Solabomi et al.; The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria; Infection and Immunity, vol. 76, No. 8; Aug. 2008; p. 3817-3823.
Sullivan et al.; Accelerated vaccination for Ebola virus haemorrhagic fever in non-human primates; Nature; vol. 424; Aug. 7, 2003; p. 681-684.
Sullivan et al.; Immune Protecttion of Nonhuman Primates against Ebola Virus with Single Low-Dose Adenovirus Vectors Encoding Modified GPs; PLoS Medicine; Jun. 2006; vol. 3, Issue 6; p. 865-873.
Tatsis et al.; A CD46-binding Chimpanzee Adenovirus Vector as a Vaccine Carrier; Molecular Therapy; vol. 15, No. 3; 608-617; Mar. 2007.
Tolunaga et al.; Physical mapping of the genome and sequence analysis at the inverted terminal repetition of adenovirus type 4 DNA; Gene, 18 (1982) 329-334.
Van Bergen et al.; Replication of origin containing adenovirus DNA fragments that do not carry the terminal protein; Nucleic Acids Research; vol. 11, No. 7, 1983; p. 1975-1989.
Vemula et al.; Production of adenovirus vectors and their use as a delivery system for influenza vaccines; Expert Opin Biol Ther: Oct. 2010 ; 10(10): 1469-1487.
Vogels et al.; Replication-Deficient Human Adenovirus Type 35 Vectors for Gene Transfer and Vaccination: Efficient Human Cell Infection and Bypass of Preexisting Adenovirus Immunity; Journal of Virology, vol. 77, No. 15; Aug. 2003; p. 8263-8271.
Wang et al.; Adenovirus sequences required for replication in vivo; Necleic Acids Research; vol. 13, No. 14; 1985; p. 5173-5187.
Zhou et al.; A Chimpanzee-Origin Adenovirus Vector Expressing the Rabies Virus Glycoprotein as an Oral Vaccine Against Inhalation Infection with Rabies Virus; Molecular Therapy, vol. 14, No. 5, Nov. 2006; p. 662-672.
PCT International Preliminary Report on Patentability, PCT/EP2013/054846 dated May 9, 2014.
Roberts et al., Hexon-chimaeric adenovirus serotype 5 vectors circumvent pre-existing anti-vector immunity, Nature, 2006, pp. 239-243, vol. 441, No. 7090.
Kinchington et al., Sequence changes in human adenovirus type 5 DNA polymerase associated with resistance to the broad spectrum antiviral cidovir, Antiviral research, 2002, pp. 83-94. vol. 56, No. 1.
He et al., 5/35 Fiber-Modified Conditionally Replicative Adenovirus Armed with p53 Shows Increased Tumor Suppressing Capacity to Breast Cancer Cells, Human Gene Therapy, 2011.
Silver et al., Transduction and oncolytic profile of a potent replication-competent Adenovirus 11p vector (RCAd11pGFP) in colon carcinoma cells, PLOS ONE 6, pp. 1-12, vol. 3, e17532.
Kaneko et al., Analysis of the complete genome sequence of epidemic keratoconjunctivitis-related human adenovirus type 8, 19, 37 and a novel serotype, Journal of General Virology, 2009, pp. 1471-1476, vol. 90.
PCT International Search Report, PCT/EP2013/054846 dated Jun. 11, 2013.
Kruse & Patterson—Tissue Culture (Academic Press 1973).
Sambrook et al—Molecular Cloning, a Laboratory Manual (Spring Harbor Press 1989).
Zhou et al.; A Universal Influenza A Vaccine Based on Adenovirus Expressing Matrix-2 Ectodomain and Nucleoprotein Protects Mice From Lethal Challenge; Molecular Therapy vol. 18, No. 12; 2182-2189; Dec. 2010.

\* cited by examiner

C  Ad5.dE3.empty.ori ITR
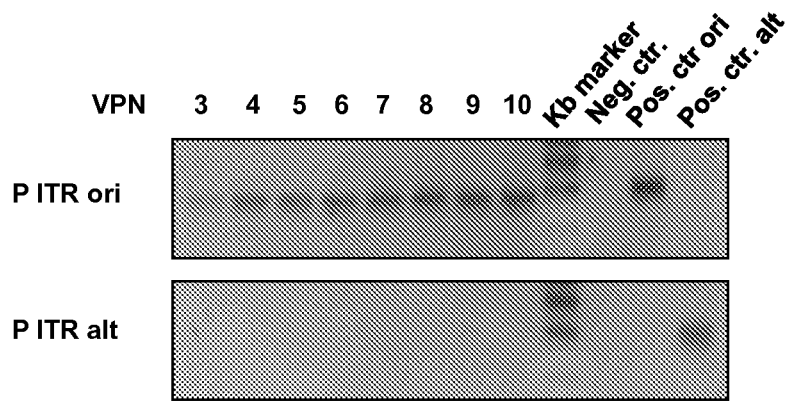
D  Ad5.dE3.empty.alt ITR
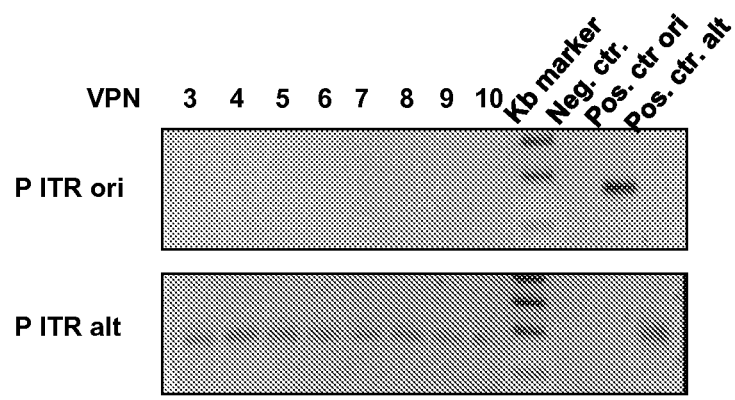
Fig. 1, cont'd

US 8,932,607 B2

BATCHES OF RECOMBINANT ADENOVIRUS WITH ALTERED TERMINAL ENDS

CROSS-REFERENCE TO RELATED APPLICATION

This application claims the benefit of U.S. Provisional Patent Application Ser. No. 61/609,678, filed Mar. 12, 2012, the disclosure of which is hereby incorporated herein in its entirety by this reference.

TECHNICAL FIELD

The disclosure relates to the field of biotechnology and medicine and to the field of gene delivery for applications in vaccination and gene therapy. More in particular, it relates to batches of recombinant adenoviral vectors.

BACKGROUND

Recombinant human and animal adenoviruses are used extensively for their application in gene therapy and vaccination. The adenovirus vector is used as a carrier for a gene of interest to be introduced into host cells, for instance, to express a gene or part thereof encoding a desired antigen to elicit an immune response.

More than 50 different human adenovirus serotypes have been identified. Of these, adenovirus serotype 5 (Ad5) has historically been studied most extensively for use as gene carrier. Recently, several other serotypes such as human Ad11, Ad26, Ad34, Ad35, Ad48, Ad49 and Ad50 and simian adenoviruses have been studied as vectors in view of lower levels of pre-existing neutralizing antibodies against these serotypes in the human population (see e.g., WO 00/70071). Promising examples of these are recombinant Ad35 (rAd35) and rAd26, which are studied in clinical trials.

The molecular biology of adenoviruses which possess a double stranded DNA genome of about 34-38 kb has been studied in detail. All adenoviruses are characterized by various inverted terminal repeats (ITRs) of about 100 bp in size (Dan et al., 2001, *Virus Genes* 22: 175-179; Liu et al., 2003, *Curr Top Microbiol Immunol* 272: 131-164), which are conserved among the serotypes of the different groups (Shinagawa et al., 1987, *Gene* 55: 85-93). The genome ends are covalently attached to the terminal protein (TP) at the 5' ends of the genome. The ITRs harbor the origin of replication (Bernstein et al., 1986, *Mol Cell Biol* 6: 2115-2124; Challberg & Rawlins, 1984, *Proc Natl Acad Sci USA* 81: 100-104; Guggenheimer et al., 1984, *Proc Natl Acad Sci USA* 81: 3069-3073; Harris & Hay, 1988, *J Mol Biol* 201: 57-67; Hay, 1985, *EMBO J* 4: 421-426; van Bergen et al., 1983, *Nucleic Acids Res* 11: 1975-1989; Wang & Pearson, 1985, *Nucleic Acids Res* 13: 5173-5187) and are crucial for DNA replication, containing binding sites for cellular proteins that promote replication and facilitating panhandle formation. The ITR sequences possess a short highly conserved canonical "core region" that ranges from nucleotide 9-18 (Liu et al., supra). The terminal 8 nucleotides, preceding this core region, however, vary between adenovirus types and isolates (Alestrom et al., 1982, *Gene* 18: 193-197; Dan et al., supra; Jacobs et al., 2004, *J Gen Virol* 85: 3361-3366; Purkayastha et al., 2005, *J Clin Microbiol* 43: 3083-3094; Rademaker et al., 2006, *J Gen Virol* 87: 553-562; Shinagawa et al., 1987, supra; Shinagawa et al., 1983, *Virology* 125: 491-495; Shinagawa & Padmanabhan, 1980, *Proc Natl Acad Sci USA* 77: 3831-3835; Tokunaga et al., 1982, *Gene* 18: 329-334; Houng et al., 2006, *J Clin Virol* 35: 381-387). While most adenoviruses display the CATCATCA (nucleotides 1-8 of SEQ ID NO:6) sequence in the terminal 8 nucleotides, several alternative sequences have been described.

The demand for recombinant adenoviruses is raising steeply in view of the variety of diseases that appear amenable for treatment or prophylaxis using these gene transfer vehicles, in combination with the large number of people affected by these diseases and ever increasing population world-wide.

For clinical batches that are intended for administration to humans, large-scale production of Recombinant Adenovirus (rAd) must be safe and efficacious, and comply with Good Manufacturing Practice (GMP) guidelines. One aspect important in this respect, is the homogeneity of such produced rAd batches.

SUMMARY

It is now surprisingly reported herein that changes were found in the sequence of the eight most terminal bases on the 5' end of the genome from certain rAds, resulting in batches that display heterogeneity with respect to these sequences.

A need remains for providing rAd batches on a large scale, which batches display improved homogeneity. The instant disclosure provides such batches, as well as methods for obtaining them. In addition, the rAd in the batches of the instant invention displays improved replication in production processes.

Provided is a composition comprising a plurality of recombinant adenovirus particles, wherein the recombinant adenovirus is a recombinant human adenovirus of serotype 5, 11a, 26, 34, 35, 48, 49 or 50, or a recombinant simian adenovirus, characterized in that the genomes of essentially all adenovirus particles in the composition comprise as the 5' terminal nucleotides the nucleotide sequence: CTATCTAT (nucleotides 1-8 of SEQ ID NO:7).

Further provided is a method for preparing a batch of (preferably at least $1 \times 10^7$) recombinant adenovirus particles that have essentially all the same nucleotide sequence in the 5' termini of their genomes, comprising: a) performing a molecular cloning step to exchange the naturally occurring 5' termini of an adenovirus genome with altered 5' termini comprising as the terminal nucleotides the nucleotide sequence: CTATCTAT (nucleotides 1-8 of SEQ ID NO:7), b) propagating in host cells the recombinant adenovirus having the altered 5' termini, and c) harvesting the recombinant adenovirus to obtain a batch of recombinant adenovirus particles that essentially all comprise as the 5' terminal nucleotides of their genomes the nucleotide sequence: CTATCTAT (nucleotides 1-8 of SEQ ID NO:7).

Also provided is a method for preparing a batch of recombinant adenovirus particles that have essentially all the same nucleotide sequence in the 5' termini of their genomes, comprising: a) performing a plaque purification of an adenovirus, wherein the recombinant adenovirus is a recombinant human adenovirus of serotype 5, 11a, 26, 34, 35, 48, 49 or 50, or a recombinant simian adenovirus, to isolate an adenovirus or recombinant adenovirus from a single plaque, wherein the adenovirus or recombinant adenovirus comprises as the 5' terminal nucleotides of its genome the nucleotide sequence: CTATCTAT (nucleotides 1-8 of SEQ ID NO:7), b) propagating in host cells a recombinant adenovirus obtained from the single plaque of step a), and c) harvesting the recombinant adenovirus to obtain a batch of recombinant adenovirus particles that essentially all comprise as the 5' terminal nucleotides of their genomes the nucleotide sequence: CTATCTAT (nucleotides 1-8 of SEQ ID NO:7).

In certain embodiments, the recombinant adenovirus in the compositions or methods hereof, is a recombinant human adenovirus, and is preferably not of human adenovirus serotype 3, 4, 7, 8, 9, 11p, 15, 21, 29, 37 or 53. In certain embodiments, the recombinant adenovirus in the compositions or methods hereof, is a recombinant human adenovirus of serotype 5, 26, 35, 49 or 50. Preferably, the recombinant adenovirus is a recombinant human adenovirus of serotype 26 or 35.

In certain embodiments, the recombinant adenovirus lacks at least a portion of the E1 region.

In certain embodiments, the recombinant adenovirus comprises a transgene.

In certain embodiments, the composition or batch of recombinant adenovirus comprises at least $1\times10^7$, preferably at least $1\times10^8$, preferably at least $1\times10^9$, preferably at least $1\times10^{10}$ recombinant adenovirus particles.

In certain embodiments, the step b) of the methods hereof is performed in a bioreactor, preferably having a volume of between about 2 liter and 20000 liter.

In certain embodiments, the methods hereof further comprise purifying the recombinant adenovirus.

In certain embodiments of the compositions or methods hereof, the recombinant adenovirus is formulated into a pharmaceutical composition.

DETAILED DESCRIPTION

Figure 1:
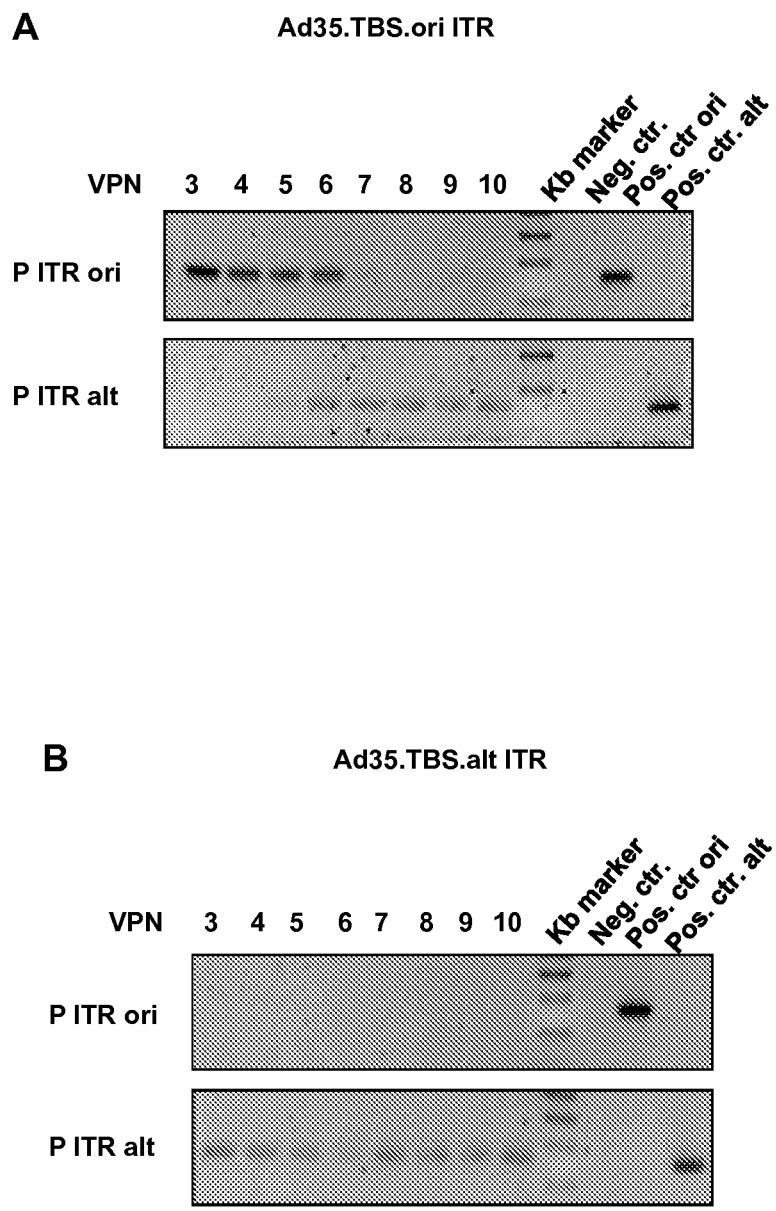
FIG. 1. Emergence of alternative ITR sequences. For details, see example 3.

It is described herein that a specific 5' terminal sequence CTATCTAT (nucleotides 1-8 of SEQ ID NO:7) is surprisingly found after several passages of various recombinant adenoviruses that initially contained other terminal sequences, and that the presence of this sequence can contribute to improved adenovirus production.

The inventors put this surprising observation into practical use by constructing and/or including an active selection step for obtaining recombinant adenoviruses of serotypes that reportedly have a different terminal sequence in their wild-type genomes, with genomes comprising as the 5' terminal nucleotides the nucleotide sequence CTATCTAT (nucleotides 1-8 of SEQ ID NO:7).

The instant disclosure therefore relates to a particular sequence (CTATCTAT nucleotides 1-8 of SEQ ID NO:7) at the terminus of the recombinant adenoviral genome and the use thereof in the production of recombinant adenoviruses. This terminal sequence may be employed in any adenovirus serotype that does not contain this sequence at the 5' terminal end of its wild-type genome.

In principle, the compositions (batches) of adenovirus hereof can contain the sequence CTATCTAT (nucleotides 1-8 of SEQ ID NO:7) at 100% of their 5' terminal genome ends (since the starting adenovirus has been actively created and/or selected hereof). In view of some natural mutations that may occasionally and randomly occur in any biological system, the actual number might be slightly below 100%, although in preferable embodiments the amount of terminal sequences other than CTATCTAT (nucleotides 1-8 of SEQ ID NO:7) is below the detection limit in the adenovirus batches hereof. Hence, hereof, essentially all of the adenoviral genomes in the compositions or batches of recombinant adenovirus particles comprise as the 5' terminal sequences the nucleotide sequence CTATCTAT (nucleotides 1-8 of SEQ ID NO:7). The term "essentially all," as used herein, refers to at least 90%, preferably at least 98%, more preferably at least 99%, still more preferably at least 99.9%, up to 100% (of the adenovirus particles in the composition). This can, for instance, be determined by methods such as PCR, which can easily detect 1 in 1000 particles, and in the compositions of recombinant adenoviral particles hereof no adenoviruses with the original terminal sequences were detectable.

A "batch" of adenovirus hereof means a composition that has been produced in one production run in a single production vessel, or alternatively it can refer to the plurality of adenovirus particles in a composition that is present in a single container (e.g., bioreactor, bag, flask, bottle, multi-dose vial, single-dose vial, syringe, etc). A batch of adenovirus hereof or a composition comprising adenovirus hereof preferably comprises at least $10^7$ recombinant adenoviral particles, and in certain embodiments comprises at least $10^8$, $10^9$, $10^{10}$, $10^{11}$, $10^{12}$, $10^{13}$, $10^{14}$, $10^{15}$, $10^{16}$, $10^{17}$, $10^{18}$, or more adenoviral particles, up to $10^{20}$ adenoviral particles (e.g., as produced in a large scale bioreactor in a single production run). A batch or composition may or may not comprise further relevant components besides the recombinant adenovirus.

The term "recombinant" for an adenovirus, as used herein implicates that it has been modified by the hand of man, e.g., it has altered terminal ends actively cloned therein and/or it comprises a heterologous gene, i.e., it is not a naturally occurring wild-type adenovirus.

Sequences herein are provided from 5' to 3' direction, as custom in the art.

An "adenovirus capsid protein" refers to a protein on the capsid of an adenovirus that is involved in determining the serotype and/or tropism of a particular adenovirus. Adenoviral capsid proteins typically include the fiber, penton and/or hexon proteins. An adenovirus of (or "based upon") a certain serotype hereof typically comprises fiber, penton and/or hexon proteins of that certain serotype, and preferably comprises fiber, penton and hexon protein of that certain serotype. These proteins are typically encoded by the genome of the recombinant adenovirus. A recombinant adenovirus of a certain serotype may optionally comprise and/or encode other proteins from other adenovirus serotypes.

A recombinant adenovirus is "based upon" an adenovirus as used herein, by derivation from the wild type, at least in sequence. This can be accomplished by molecular cloning, using the wild-type genome or parts thereof as starting material. It is also possible to use the known sequence of a wild-type adenovirus genome to generate (parts of) the genome de novo by DNA synthesis, which can be performed using routine procedures by service companies having business in the field of DNA synthesis and/or molecular cloning (e.g., Gene-Art, GenScripts, Invitrogen, Eurofins). Thus, as non-limiting examples, a recombinant adenovirus that is not based upon human Ad4 is a recombinant adenovirus that does not comprise penton, hexon and fiber of human Ad4; a recombinant adenovirus that comprises hexon, penton and fiber of Ad35 is considered a recombinant adenovirus based upon Ad35, etc.

Due to the extensive research that has been performed on adenovirus serotypes and their genomic organisation, the person skilled in the art is aware of the boundaries of the ITRs in an adenoviral genome. The sequence CTATCTAT (nucleotides 1-8 of SEQ ID NO:7) is located in the recombinant adenoviruses according to the instant disclosure at the utmost terminal ends of the genome. For instance, the upper strand of the left ITR of wt Ad5 starts with 5'-CATCATCA . . . -3'

(nucleotides 1-8 of SEQ ID NO:6) and that sequence is changed hereof to the preferred sequence 5'-CTATCTAT . . . -3' (nucleotides 1-8 of SEQ ID NO:7). The person skilled in the art is aware of the fact that at the right ITR, this sequence from 5' to 3' is located in the lower strand.

Changing the original (parental) sequence to the altered sequence hereof may be carried out by different means, which means in itself are known and routine to those of skill in the art. Examples are direct PCR generation of the sequences, or sub-cloning from original adenoviral genomes that are identified to contain the specified sequence at their termini.

When the sequence of one terminus is changed, for instance, by using molecular biology techniques in a plasmid/cosmid homologous recombination procedure (see e.g., WO 99/55132), while the other terminus remains unchanged, the resulting adenovirus will, during production and replication, copy the left or the right ITR, resulting in a mixed population with adenoviruses having only amended termini and adenoviruses with only non-amended termini (which as outlined herein, will evolve towards a population with more and more altered termini having terminal sequence CTATCTAT (nucleotides 1-8 of SEQ ID NO:7), if cultured and propagated in vitro because of the growth advantage conferred by this terminal sequence). It is preferred that a recombinant adenovirus according to the instant disclosure comprises a genome that comprises the sequence CTATCTAT (nucleotides 1-8 of SEQ ID NO:7) at both the left and right genome terminal ends.

The recombinant adenoviruses hereof thus comprise as the 5' terminal nucleotides of the genome the nucleotide sequence: CTATCTAT (nucleotides 1-8 of SEQ ID NO:7).

The vectors of the instant disclosure are recombinant adenoviruses, also referred to as recombinant adenoviral vectors. The preparation of recombinant adenoviral vectors is well known in the art.

In certain embodiments, an adenoviral vector hereof is deficient in at least one essential gene function of the E1 region, e.g., the E1a region and/or the E1b region, of the adenoviral genome that is required for viral replication. In certain embodiments, an adenoviral vector hereof is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., Scientific American Books (1992), and Ausubel et al., *Current Protocols in Molecular Biology*, Wiley Interscience Publishers, NY (1995), and other references mentioned herein.

An adenovirus hereof belongs to the family of the Adenoviridae and preferably is one that belongs to the genus *Mastadenovirus*. It can be a human adenovirus, but also an adenovirus that infects other species, including but not limited to a bovine adenovirus (e.g., bovine adenovirus 3, BAdV3), a canine adenovirus (e.g., CAdV2), a porcine adenovirus (e.g., PAdV3 or 5), or a simian adenovirus (which includes a monkey adenovirus and an ape adenovirus, such as a chimpanzee adenovirus). Preferably, the adenovirus is a human adenovirus (HAdV, or AdHu; in the instant disclosure a human adenovirus is meant if referred to Ad without indication of species, e.g., the brief notation "Ad5" means the same as HAdV5, which is human adenovirus serotype 5) or a simian adenovirus such as chimpanzee adenovirus (ChAd, AdCh, or SAdV).

Preferably, the recombinant adenovirus hereof is an adenovirus for which the wild type has been reported to have a different sequence (than CTATCTAT (nucleotides 1-8 of SEQ ID NO:7), e.g., the often occurring sequence CATCATCA (nucleotides 1-8 of SEQ ID NO:6) at the 5' terminal end. The reported or inferred 5' terminal 8 nucleotides of various adenovirus serotypes are depicted in Table I. U.S. 2009/227000 reports an Ad11p having CTATCTAT (nucleotides 1-8 of SEQ ID NO:7) at the 5' terminal end. Most advanced studies have been performed using human adenoviruses, and human adenoviruses are preferred according to certain aspects hereof. In certain preferred embodiments, the recombinant adenovirus hereof is based upon a human adenovirus, and is not based upon a human adenovirus serotype 3, 4, 7, 8, 9, 11p, 15, 21, 29, 37 or 53. In preferred embodiments, the recombinant adenovirus is based upon a human adenovirus serotype 1, 2, 5, 6, 10, 11a, 12, 14, 16, 17, 18, 19, 22, 26, 28, 31, 34, 35, 36, 40, 41, 46, 48, 49, 50, 53, 54, 55, 56 or 57. More preferably, the recombinant adenovirus is based upon a human adenovirus serotype 5, 11a, 26, 34, 35, 48, 49 or 50. According to a particularly preferred embodiment hereof, an adenovirus is a human adenovirus of one of the serotypes 26, 35, 48, 49 or 50. An advantage of these serotypes is a low seroprevalence and/or low pre-existing neutralizing antibody titers in the human population. The most preferred serotypes for the recombinant adenovirus are human serotype 35 or human serotype 26, both of which are evaluated in clinical trials. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) *J Virol* 77(15): 8263-71. Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g., US6083716; WO 2005/071093; WO 2010/086189; WO 2010085984; Farina et al., 2001, *J Virol* 75: 11603-13; Cohen et al., 2002, *J Gen Virol* 83: 151-55; Kobinger et al., 2006, *Virology* 346: 394-401; Tatsis et al., 2007, *Molecular Therapy* 15: 608-17; see also review by Bangari and Mittal, 2006, *Vaccine* 24: 849-62; and review by Lasaro and Ertl, 2009, *Mol Ther* 17: 1333-39). Hence, in other preferred embodiments, the recombinant adenovirus hereof is based upon a simian adenovirus, e.g., a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

The sequences of most of the human and non-human adenoviruses mentioned above are known, and for others can be obtained using routine procedures.

A recombinant adenovirus hereof may be replication-competent or replication-deficient.

In certain embodiments, the adenovirus is replication deficient, e.g., because it contains a deletion in the E1 region of the genome. As known to the skilled person, in case of deletions of essential regions from the adenovirus genome, the functions encoded by these regions have to be provided in trans, preferably by the producer cell, i.e., when parts or whole of E1, E2 and/or E4 regions are deleted from the adenovirus, these have to be present in the producer cell, for instance, integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as "packaging cell" or "complementing cell" or "host cell") that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g., 911 or PER.C6 cells (see U.S. Pat. No. 5,994,128), E1-transformed amniocytes (See EP Patent 1230354), E1-transformed A549 cells (see e.g., WO 98/39411, U.S. Pat. No. 5,891,690), GH329:HeLa (Gao et al., 2000, *Human Gene Therapy* 11: 213-219), 293, and the like. In certain embodiments, the producer cells are, for instance, HEK293 cells, or PER.C6 cells, or 911 cells, or IT293SF cells, and the like.

For E1-deficient adenoviruses that are not derived from subgroup C or E adenoviruses, it is preferred to exchange the E4-orf6 coding sequence of the non-subgroup C or E adenovirus with the E4-orf6 of an adenovirus of subgroup C such as Ad5. This allows propagation of such adenoviruses in well known complementing cell lines that express the E1 genes of Ad5, such as, for example, 293 cells or PER.C6 cells (see, e.g., Havenga et al., 2006, *J. Gen. Virol.* 87: 2135-2143; WO 03/104467, incorporated in its entirety by reference herein).

In alternative embodiments, there is no need to place a heterologous E4orf6 region (e.g., of Ad5) in the adenoviral vector, but instead the E1-deficient non-subgroup C or E vector is propagated in a cell line that expresses both E1 and a compatible E4orf6, e.g., the 293-ORF6 cell line that expresses both E1 and E4orf6 from Ad5 (see e.g., Brough et al., 1996, *J Virol* 70: 6497-501 describing the generation of the 293-ORF6 cells; Abrahamsen et al., 1997, *Virol* 71: 8946-51 and Nan et al., 2003, *Gene Therapy* 10: 326-36 each describing generation of E1 deleted non-subgroup C adenoviral vectors using such a cell line).

Alternatively, a complementing cell that expresses E1 from the serotype that is to be propagated can be used (see e.g., WO 00/70071, WO 02/40665).

For subgroup B adenoviruses, such as Ad35, having a deletion in the E1 region, it is preferred to retain the 3' end of the E1B 55K open reading frame in the adenovirus, for instance, the 166 bp directly upstream of the pIX open reading frame or a fragment comprising this such as a 243 bp fragment directly upstream of the pIX start codon (marked at the 5' end by a Bsu36I restriction site in the Ad35 genome), since this increases the stability of the adenovirus because the promoter of the pIX gene is partly residing in this area (see, e.g., Havenga et al., 2006, *J. Gen. Virol.* 87: 2135-2143; WO 2004/001032, incorporated by reference herein).

"Heterologous nucleic acid" (also referred to herein as "transgene") in adenoviruses hereof is nucleic acid that is not naturally present in the adenovirus. It is introduced into the adenovirus, for instance, by standard molecular biology techniques. It may in certain embodiments encode a protein of interest or part thereof. It can, for instance, be cloned into a deleted E1 or E3 region of an adenoviral vector. A transgene is generally operably linked to expression control sequences. This can, for instance, be done by placing the nucleic acid encoding the transgene(s) under the control of a promoter. Further regulatory sequences may be added. Many promoters can be used for expression of a transgene(s), and are known to the skilled person. A non-limiting example of a suitable promoter for obtaining expression in eukaryotic cells is a CMV-promoter (U.S. Pat. No. 5,385,839), e.g., the CMV immediate early promoter, for instance, comprising nt. −735 to +95 from the CMV immediate early gene enhancer/promoter. A polyadenylation signal, for example, the bovine growth hormone polyA signal (U.S. Pat. No. 5,122,458), may be present behind the transgene(s).

In certain embodiments, it may be desired to express more than one protein from a single adenovirus, and in such cases more coding sequences may be linked to form a single transcript from a single expression cassette or may be present in two separate expression cassettes cloned in different parts of the adenoviral genome.

The identity of the transgene is not material for the instant invention, which is suitable for adenoviruses comprising any transgene. Suitable transgenes are well known to the skilled person, and, for instance, may include transgene open reading frames, for instance, open reading frames coding for polypeptides that have a therapeutic effect, e.g., for gene therapy purposes, or polypeptides against which an immune response is desired when the rAd vector is used for vaccination purposes. Particularly preferred heterologous nucleic acids are genes of interest encoding antigenic determinants towards which an immune response needs to be raised. Such antigenic determinants are also typically referred to as antigens. Any desired antigen can be encoded by the adenovirus vector. In typical embodiments hereof, antigens are peptides, polypeptides or proteins from organisms that may cause a disease or condition. Therefore, in a further preferred embodiment, the heterologous nucleic acid of interest encodes an immunogenic determinant. More preferably, the immunogenic determinant is an antigen from a bacterium, a virus, yeast or a parasite. The diseases caused by such organisms are generally referred to as "infectious disease" (and are thus not limited to organisms that "infect" but also include those that enter the host and cause a disease). So-called "self-antigens," e.g., tumour antigens, also form part of the state of the art, and may be encoded by heterologous nucleic acids in the recombinant adenoviruses according to the instant disclosure. Non-limiting examples from which the antigenic determinants (or antigens) are taken are malaria-causing organisms, such as *Plasmodium falciparum*, tuberculosis-causing organism such as *Mycobacterium tuberculosis*, yeasts, or viruses. In other preferred embodiments, antigens from viruses such as flaviviruses (e.g., West Nile Virus, Hepatitis C Virus, Japanese Encephalitis Virus, Dengue Virus), ebola virus, Human Immunodeficiency Virus (HIV), and Marburg virus may be used in compositions according to the instant disclosure. In one embodiment, the antigen is the CS protein or immunogenic part thereof from *P. falciparum* (for examples, of adenovirus vectors encoding CS, see e.g., Havenga et al., 2006, *J. Gen. Virol.* 87: 2135-2143; Ophorst et al., 2007, *Vaccine* 25:1426-36; WO 2004/055187, all incorporated in their entirety by reference herein). In another embodiment, the antigenic determinant is a protein of one antigen-, or a fusion protein of several antigens from *M. tuberculosis*, such as the Ag85A, Ag85B and/or the TB10.4 proteins or immunogenic part(s) thereof (see for the construction and production of such TB vaccine viruses e.g., WO 2006/053871, incorporated by reference herein). In yet another embodiment, the antigenic determinant is a viral glycoprotein or immunogenic part thereof, such as GP from a filovirus, such as ebola virus or Marburg virus (e.g., Sullivan et al., (2003) *Nature* 424 (6949): 681-684; Sullivan, et al., (2006) *PLoS Med* 3(6): e177; Geisbert et al., (2011) *J Virol* 85: 4222-4233). In yet further embodiments, the immunogenic determinant is from an HIV protein such as gag, pol, env, nef, or variants thereof (for examples, of adenovirus based HIV vaccines, see e.g., WO 2009/026183, WO 2010/096561, WO 2006/120034, WO 02/22080, WO 01/02607). In other embodiments, the antigenic determinant is a HA, NA, M, or NP protein, or immunogenic part of any of these, from influenza virus (e.g., Zhou et al., 2010, *Mol Ther* 18:2182-9; Hu et al., 2011, *Virus Res* 155: 156-62; review by Vemula and Mittal, 2010, *Expert Opin Biol Ther* 10: 1469-87). In other embodiments, the antigenic determinant is a HA protein or immunogenic part thereof from a measles virus (e.g., WO 2004/037294). In other embodiments, the antigenic determinant is rabies virus glycoprotein (e.g., Zhou et al., 2006, *Mol Ther* 14: 662-672).

Also provided is a method for preparing a batch of recombinant adenovirus particles that have essentially all identical nucleotide sequences in the 5' termini of their genomes, the method comprising: a) performing a molecular cloning step to exchange the naturally occurring 5' termini of an adenovirus genome with altered 5' termini comprising as the terminal nucleotides the nucleotide sequence: CTATCTAT (nucleotides 1-8 of SEQ ID NO:7), b) propagating in host cells the recombinant adenovirus having the altered 5' termini, and c) harvesting the recombinant adenovirus to obtain a batch of recombinant adenovirus particles that essentially all comprise as the 5' terminal nucleotides of their genomes the nucleotide sequence: CTATCTAT (nucleotides 1-8 of SEQ ID NO:7). In this preferred aspect, the 5' termini of the genomes are actively changed by molecular cloning techniques, which are as such well known and routine to the person skilled in the art of molecular biology. The identification of this advantageous CTATCTAT (nucleotides 1-8 of SEQ ID NO:7) terminal sequence herein, renders this active step possible. This step is advantageous whenever any adenovirus having a different 5' terminal sequence (i.e., not CTATCTAT (nucleotides 1-8 of SEQ ID NO:7)) is used as starting material or basis for generation of a (batch or composition of) recombinant adenovirus hereof, e.g., for any of the preferred serotypes hereof as indicated herein. An advantage is the control and certainty that from the outset the desired CTATCTAT (nucleotides 1-8 of SEQ ID NO:7) sequence is present in all genomes of the seed adenovirus for step b), and in view of the stability of this sequence as reported herein, the resulting batches of adenovirus in step c) will comprise adenoviral particles that essentially all have the same desired 5' terminal sequence.

However, as an alternative to the molecular cloning route, one could now also use the naturally induced variation and select for an adenovirus that has the altered sequence CTATCTAT (nucleotides 1-8 of SEQ ID NO:7) at its terminus, to obtain the requisite starting material with stable 5' termini for propagation into batches of adenovirus at any desired scale. Thus, as an alternative embodiment, also provided is a method for preparing a batch of recombinant adenovirus particles that have essentially all identical nucleotide sequences in the 5' termini of their genomes, comprising: a) performing a plaque purification of an adenovirus, not being human adenovirus serotype 3, 4, 7, 8, 9, 11p, 15, 21, 29, 37 or 53 or a recombinant form thereof, to isolate an adenovirus or recombinant adenovirus from a single plaque, wherein the adenovirus or recombinant adenovirus comprises as the 5' terminal nucleotides of its genome the nucleotide sequence: CTATCTAT (nucleotides 1-8 of SEQ ID NO:7), b) propagating in host cells a recombinant adenovirus obtained from the single plaque of step a), and c) harvesting the recombinant adenovirus to obtain a batch of recombinant adenovirus particles that essentially all comprise as the 5' terminal nucleotides of their genomes the nucleotide sequence: CTATCTAT (nucleotides 1-8 of SEQ ID NO:7). Here, the active step is the preparation of a single plaque of (recombinant) adenovirus and testing/confirming that the genome thereof comprises at its 5' terminal end the desired sequence CTATCTAT (nucleotides 1-8 of SEQ ID NO:7). The skilled person will appreciate that step a) of this embodiment may be performed with either an already recombinant adenovirus, or with still a wild-type adenovirus isolate, wherein in the latter case prior to step b) a step is performed to obtain the recombinant adenovirus (e.g., by cloning, to introduce the transgene in the genome). A step of plaque purification to ensure that the starting material for further work is homogeneous and derived from a single isolate can be performed using entirely routine procedures for the skilled person in the field of adenovirus manipulation. Actively selecting for a (recombinant) adenovirus that comprises as the 5' terminal nucleotides of its genome the nucleotide sequence CTATCTAT (nucleotides 1-8 of SEQ ID NO:7) had not been described before, and prior to the instant disclosure this would not have made any sense either. To the contrary, the identification of this sequence would have been seen as an anomaly and the plaque would have been disposed of as having a genetic alteration prior to the instant invention. It is the merit of the instant invention to select for such (recombinant) adenovirus as starting material to ensure genetic stability, resulting in batches of recombinant adenovirus that essentially all comprise the same desired 5' terminal nucleotides in their genomes. The recombinant adenovirus hereof has potentially improved replication characteristics.

A host cell according to the methods hereof can be a packaging cell, which may complement for deficiencies in the recombinant adenoviral genome, e.g., E1. Steps b) and c) of the methods hereof are standard and routine steps in the preparation of batches of recombinant adenovirus, well known to the skilled person.

In certain embodiments, step b) of these methods is performed in a bioreactor, which may have a volume of between about 1 liter to about 20000 liter. This enables obtaining sufficient quantities of the desired adenovirus compositions for use at industrial scale. The term "about" for numerical values as used in the present disclosure means the value±10%. In certain embodiments, the working volume is between 10 L and 10000 L, e.g., between 20 L and 2000 L. The working volume is the effective culture volume in the bioreactor. The volume of the bioreactor may be chosen by the skilled person depending on the actual demand. The instant disclosure ensures that the final product will have the same terminal ends for essentially all adenovirus particles in batches so produced, i.e., be genetically homogeneous, which is desired for a pharmaceutical product.

Most large-scale suspension cultures are operated as batch or fed-batch processes because they are the most straightforward to operate and scale up. Nowadays, continuous processes based on perfusion principles are becoming more common and are also suitable (see e.g., WO 2010/060719, and WO 2011/098592, both incorporated by reference herein, which describe suitable methods for obtaining and purifying large amounts of recombinant adenoviruses).

Producer cells are cultured to increase cell and virus numbers and/or virus titers. Culturing a cell is done to enable it to metabolize, and/or grow and/or divide and/or produce virus of interest hereof. This can be accomplished by methods as such well known to persons skilled in the art, and includes but is not limited to providing nutrients for the cell, for instance, in the appropriate culture media. Suitable culture media are well known to the skilled person and can generally be obtained from commercial sources in large quantities, or custom-made according to standard protocols. Culturing can be done, for instance, in dishes, roller bottles or in bioreactors, using batch, fed-batch, continuous systems and the like. Suitable conditions for culturing cells are known (see e.g., Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Typically, the adenovirus will be exposed to the appropriate producer cell in a culture, permitting uptake of the virus. Usually, the optimal agitation is between about 50 and 300 rpm, typically about 100-200, e.g., about 150, typical DO is 20-60%, e.g., 40%, the optimal pH is between 6.7 and 7.7, the optimal temperature between 30 and 39° C., e.g., 34-37° C., and the optimal MOI between 5 and 1000, e.g., about 50-300. Typically, adenovirus infects producer cells spontaneously, and bringing the producer cells into contact with rAd particles is sufficient for infection of the cells. Generally, an adenovirus seed stock is added to the culture to initiate infection, and subsequently the adenovirus propagates in the producer cells. This is all routine for the person skilled in the art. Such an adenovirus seed stock hereof comprises recombinant adenovirus particles wherein the genomes of essentially all adenovirus particles in the seed stock comprise as the 5' terminal nucleotides the sequence CTATCTAT (nucleotides 1-8 of SEQ ID NO:7).

After infection of an adenovirus, the virus replicates inside the cell and is thereby amplified, a process referred to herein as propagation of adenovirus. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g., U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have, for instance, been discussed in WO 98/22588, p. 28-35. Useful methods in this respect are, for example, freeze-thaw, solid shear, hypertonic and/or hypotonic lysis, liquid shear, sonication, high pressure extrusion, detergent lysis, combinations of the above, and the like. In one embodiment hereof, the cells are lysed using at least one detergent. Use of a detergent for lysis has the advantage that it is an easy method, and that it is easily scalable.

Detergents that can be used, and the way they are employed, are generally known to the person skilled in the art.

Several examples are, for instance, discussed in WO 98/22588, p. 29-33. Detergents can include anionic, cationic, zwitterionic, and nonionic detergents. The concentration of the detergent may be varied, for instance, within the range of about 0.1%-5% (w/w). In one embodiment, the detergent used is Triton X-100.

Nuclease may be employed to remove contaminating, i.e., mostly from the producer cell, nucleic acids. Exemplary nucleases suitable for use in the instant disclosure include Benzonase®, Pulmozyme®, or any other DNase and/or RNase commonly used within the art. In preferred embodiments, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g., U.S. Pat. No. 7,326,555; Goerke et al., 2005, Biotechnology and bioengineering, Vol. 91: 12-21; WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in, for instance, WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as, for instance, discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is, for instance, possible to purify adenoviruses by anion exchange chromatography steps, see, for instance, WO 2005/080556. Many other adenovirus purification methods have been described and are within the reach of the skilled person. Further methods for producing and purifying adenoviruses are disclosed in, for example, WO 00/32754, WO 04/020971, U.S. Pat. No. 5,837,520, U.S. Pat. No. 6,261,823, and WO 2006/108707, all incorporated by reference herein.

For administering to humans, the invention may employ pharmaceutical compositions comprising the rAd and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified rAd preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g., pH 5.0 to 7.5. The rAd typically is in a solution having a suitable buffer, and the solution of rAd may also contain a salt. Optionally stabilizing agent may be present, such as albumin. In certain embodiments, detergent is added. In certain embodiments, rAd may be formulated into an injectable preparation. These formulations contain effective amounts of rAd, are either sterile liquid solutions, liquid suspensions or lyophilized versions and optionally contain stabilizers or excipients. An adenovirus vaccine can also be aerosolized for intranasal administration (see e.g., WO 2009/117134).

For instance, adenovirus may be stored in the buffer that is also used for the Adenovirus World Standard (Hoganson et al., Development of a stable adenoviral vector formulation, *Bioprocessing* March 2002, p. 43-48): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Many other buffers can be used, and several examples of suitable formulations for the storage and for pharmaceutical administration of purified (adeno)virus preparations can, for instance, be found in European Patent No. 0853660, U.S. Pat. No. 6,225,289 and in International Patent Applications WO 99/41416, WO 99/12568, WO 00/29024, WO 01/66137, WO 03/049763, WO 03/078592, WO 03/061708.

In certain embodiments, a composition comprising the adenovirus further comprises one or more adjuvants. Adjuvants are known in the art to further increase the immune response to an applied antigenic determinant, and pharmaceutical compositions comprising adenovirus and suitable adjuvants are, for instance, disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors hereof. Examples of suitable adjuvants include aluminium salts such as aluminium hydroxide and/or aluminium phosphate; oil-emulsion compositions (or oil-in-water compositions), including squalene-water emulsions, such as MF59 (see e.g., WO 90/14837); saponin formulations, such as, for example, QS21 and Immunostimulating Complexes (IS-COMS) (see e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g., by using heterologous nucleic acid that encodes a fusion of the oligomerization domain of C4-binding protein (C4 bp) to the antigen of interest (e.g., Solabomi et al., 2008, *Infect Immun* 76: 3817-23). In certain embodiments the compositions hereof comprise aluminium as an adjuvant, e.g., in the form of aluminium hydroxide, aluminium phosphate, aluminium potassium phosphate, or combinations thereof, in concentrations of 0.05-5 mg, e.g., from 0.075-1.0 mg, of aluminium content per dose.

In other embodiments, the compositions do not comprise adjuvants.

Adenovirus compositions may be administered to a subject, e.g., a human subject. The total dose of the adenovirus provided to a subject during one administration can be varied as is known to the skilled practitioner, and is generally between $1 \times 10^7$ viral particles (vp) and $1 \times 10^{12}$ vp, preferably between $1 \times 10^8$ vp and $1 \times 10^{11}$ vp, for instance, between $3 \times 10^8$ and $5 \times 10^{10}$ vp, for instance, between $10^9$ and $3 \times 10^{10}$ vp.

Administration of adenovirus compositions can be performed using standard routes of administration. Non-limiting embodiments include parenteral administration, such as by injection, e.g., intradermal, intramuscular, etc., or subcutaneous or transcutaneous, or mucosal administration, e.g., intranasal, oral, and the like. In one embodiment a composition is administered by intramuscular injection, e.g., into the deltoid muscle of the arm, or vastus lateralis muscle of the thigh. The skilled person knows the various possibilities to administer a composition, e.g., a vaccine in order to induce an immune response to the antigen(s) in the vaccine.

A subject, as used herein, preferably is a mammal, for instance, a rodent, e.g., a mouse, or a non-human-primate, or a human. Preferably, the subject is a human subject.

It is also possible to provide one or more booster administrations of one or more adenovirus vaccines. If a boosting vaccination is performed, typically, such a boosting vaccination will be administered to the same subject at a moment between one week and one year, preferably between two weeks and four months, after administering the composition to the subject for the first time (which is in such cases referred to as "priming vaccination"). In alternative boosting regimens, it is also possible to administer different vectors, e.g., one or more adenoviruses of different serotype, or other vectors such as MVA, or DNA, or protein, to the subject as a priming or boosting vaccination.

The invention is further described in the following illustrative examples.

EXAMPLES

Methods

Plasmids:

The alternative ITR sequence was introduced into the left ITR by cloning into pAdapt and into the right ITR by cloning into pBr plasmids for Ad35 and Ad5, respectively, (see e.g., Havenga M. et al., 2006, *J. Gen. Virol.* 87: 2135-2143; Havenga M. et al., 2001, *J. Virol.* 75: 3335-3342). To introduce the alternative ITR sequence into the left ITR, a fusion PCR was performed using a forward primer containing a ScaI site (GTGACTGGTGAGTACTC [SEQ ID NO:1]), a reverse primer containing an AvrII site (GACCACCTAGGCTGAC [SEQ ID NO:2]) and fusion forward and reverse primers harboring the alternative ITR sequence (alt ITR for 1: TTAATTAATCGATCTATCTATATAATATACCTTATAG (SEQ ID NO:3), alt ITR for 2: GATCTATC-TATATAATATACCTTATAGATGGAATGG (SEQ ID NO:4), alt ITR rev: ATTATATAGATAGATCGATTAAT-TAATTCGAACCC (SEQ ID NO:5)). Two partly overlapping ITR forward primers were used in the PCR for one of the fusion PCR fragments to increase the PCR efficiency on an extremely AT rich region in the template. The fusion PCR product was first subcloned into the pTopo vector to facilitate sucloning and then inserted into pAdapt35 plasmid via the AvrII and ScaI sites with the indicated transgenes.

To introduce the alternative ITR sequence into the right ITR, a fusion PCR was performed using a forward primer containing an NdeI site and a reverse primer containing an NruI site and fusion forward and reverse primers harboring the alternative ITR sequence using the same fusion PCR strategy as described for the left ITR. The fusion PCR product was then subcloned into pTopo and subsequently into pBR.Ad35.PR.dE3 orf6/7 plasmid using NdeI and NruI.

To generate Ad5 vectors with alternative ITRs the same strategy as described above was used.

Cell Culture:

PER.C6 cells (Fallaux et al., 1998) were maintained in Dulbecco's modified Eagle's medium (DMEM) with 10% fetal bovine serum (FBS), supplemented with 10 mM $MgCl_2$. A549, HEK293, Hep2, HeLa and MRC5 cells were obtained from ATCC and maintained in DMEM with 10% FBS.

Adenovirus Generation, Infections and Passaging:

If not otherwise stated, all viruses were generated in PER.C6 by single or double homologous recombination and produced as previously described (Havenga et al., 2006). Briefly, plasmids were transfected in PER.C6 using Lipofectamine according to the instructions provided by the manufacturer (Life Technologies). Cells were harvested one day after full CPE, freeze-thawed, centrifuged for 5 min at 3,000 rpm, and stored at −20° C. Of the crude lysate, 3 to 5 ml was used to inoculate 4×T175 triple-layer flasks containing 70% confluent layers of PER.C6 cells. The virus was purified using a two-step CsCl purification method. Finally, the virus was stored in aliquots at =85° C.

To investigate the switch from the original to an alternative ITR sequence, the different viruses were passaged serially using either crude virus material after plaque purification or purified virus batches as described above. To this end, cells were infected with the respective viral vector. One day after full CPE, the cells and the supernatant were harvested and frozen. The viral particles were released from the cells by thawing and this crude virus material was used to infect new cells.

Viral DNA Isolation from Infected Cells:

DNA isolations for the ITR-specific PCR were performed as follows. Viral particles were released from crude virus material by repeated freeze-thaw cycles. Afterwards, host cell DNA was removed by DNAse I treatment. Viral particles were disrupted by Incubation with 10% SDS and treated with proteinase K. Viral DNA was subsequently purified using the GeneClean Spin Kit (MP Biochemicals) and used for PCR analysis.

Crude lysate was used to isolate DNA for ITR sequence analysis. For this purpose, DNA was isolated by PEG isolation from 20 ml of crude cell lysate, lysed by consecutive freeze-thaw cycles and treated with DNAse I (0.01 mg/ml Roche) and Rnase T1 (10 U/ml Roche), followed by NaCl inactivation (1M). Viral particles were precipitated using 10% PEG 6000 (BDH iochemical) on ice for 1 h, followed by a centrifugation step at 9000×g and resuspended in 1 ml of SM buffer (0.1M NaCl, 8 mM MgSO4, 50 mM Tris HCl pH 7.5, 0.002% gelatine). Viral capsid proteins were disrupted using 10% SDS and proteinase K treatment and the DNA was extracted by phenol-chloroform precipitation. Full length DNA was digested by EcoRI (Ad26), SphI (Ad48, Ad5), AgeI (Ad49, Ad11), NheI (Ad50) and finally sequenced by Baseclear, Leiden.

ITR-Specific PCR

Since the ITR regions are AT rich, locked nucleic acid (LNA) primers were used to assure sufficient primer binding to the template. Primers were purchased from Eurogentech. The following primers were used. Lower case letter indicate LNA nucleotides. ori.ITR: CatcaTcaATAATATACC [SEQ ID NO:6], Ad35 alt ITR: CtatcTatATAATATACC [SEQ ID NO:7], Ad35 left ITR rev: CTAAGTAGTTCCGT-GAGAAAAG [SEQ ID NO:8]. Ad35 right ITR forward: GGTACGTCACATCCCATTAA [SEQ ID NO:9], Ad5 left ITR rev: CACTTTTGCCACATCCGTC [SEQ ID NO:10], Ad5 right ITR for: CCCACGTTACGTCACTTC [SEQ ID NO:11]. PCR products were analyzed on an agarose gel.

Replication Kinetics by qPCR

Replication kinetics were analyzed by infection of 293 and PER.C6 cells using 1000 VP/cell for 3 hours and subsequently washed. Presence of viral particles in cells and supernatant were analyzed at indicated time points post infection by a VP qPCR. To this end, infected cells were lysed using 0.5% Triton X-100 (Sigma), incubated at −80 degrees for 1 hour and thawed.

A qPCR specific for the CMV promoter, present in all used adenoviral vectors was performed using gene expression master mix (Applied Biosystems) according to manufacturer's recommendations. Primer/probe combination sequences are: CMV for: TGGGCGGTAGGCGTGTA [SEQ ID NO:12], CMV rev: CGATCTGACGGTTCACTAAACG [SEQ ID NO:13], Probe 5'-VIC-TGGGAGGTC-TATATAAGC-MGB-NFQ-3' [SEQ ID NO:14], purchased from Applied Biosystems. To determine the amount of viral particles in the individual samples, a standard curve was generated.

Sequence Alignments

Adenovirus ITR sequences were obtained from BLAST search. The alignment was created using CLC software. Alignments are based on published sequences. However, for some of the published sequences, the ITRs have not specifically been sequenced. Instead, conservation across subtypes was assumed, which might lead to an overrepresentation of the conserved CATCATCA (nucleotides 1-8 of SEQ ID NO:6) sequence. In case several sequences for one adenovirus serotype were published, they were only included if they differed from each other in the terminal 8 nucleotides.

Example 1

Detection of an Alternative ITR Sequence During Production of an Ad35 Vaccine Vector on PER.C6 Cells For generation of an Ad35 vaccine vector expressing *Mycobacterium tuberculosis* antigens Ag85A, Ag85B, and TB10.4 antigens as previously described (WO 2006/053871; (Radosevic et al., 2007, *Infect. Immun.* 75: 4105-4115), PER.C6 cells were transfected with linearized plasmids, yielding the Ad35.TBS virus, capable of replication in PER.C6 cells.

Prior to production, two consecutive plaque purifications ensure derivation of the virus seed from a single genetically stable clone. The obtained virus was characterized by identity PCR and Western Blot at different stages of the production process and completely sequenced before usage as a seed virus for large-scale production.

The genome sequence was stable and thus identical to the genome encoded by the rescue plasmids with the exception of the terminal 8 nucleotides at the left and the right ITR. The plasmid encoded sequence CATCATCA (nucleotides 1-8 of SEQ ID NO:6), named original ITR sequence in the following, switched to the sequence CTATCTAT (nucleotides 1-8 of SEQ ID NO:7), termed alternative ITR sequence, resulting in 6 nucleotide changes in comparison to the plasmid sequence. This finding was surprising since adenoviral genomes are considered to be highly stable thereby contributing to their suitability as vaccine vectors.

To investigate the inconsistency in the terminal ITR sequence further, we sequenced the ITRs at different steps during the production of the vaccine vector: This analysis revealed that the original ITR sequence was still present at five passages after plaque purification (VPN 5). However, we also detected a sequence with subpeaks indicating a mixing sequence at passage number 5 of a different production process. Except for the subpeaks within the terminal 8 nucleotides, the remaining sequence did not display any inconsistencies. At VPN 6 the sequence is mixed, likely being composed of approximately the same proportion of the original and the alternative sequence and turning into a distinct alternative sequence at VPN 7.

Example 2

ITR Heterogeneity Occurs for Different Ad35 Vectors as Well as for Wild-Type Virus To address whether the observed phenomenon is a negligible event and to examine the frequency of the switch from the original CATCATCA (nucleotides 1-8 of SEQ ID NO:6) to the alternative CTATCTAT (nucleotides 1-8 of SEQ ID NO:7) ITR sequence, we analyzed four plaques originating from the same virus rescue. Viruses propagated from all plaques switched to an alternative ITR sequence upon repeated passaging.

Furthermore, alternative ITRs were observed during passaging of Ad35 vectors expressing different transgenes and independent of a partial deletion of the pIX promoter (Table II).

Furthermore, we do not only see mixing sequences for Ad35 based vectors, but also for the Ad35 wild-type virus, excluding a vector artifact.

Example 3

The Alternative ITR Sequence is Stable in Ad35.TBS Over 10 Viral Passages

To address whether the switch to the alternative ITR sequence is stable over several viral passages, we constructed an Ad35.TBS harboring either original or alternative ITR sequences, termed Ad35.TBS.ori ITR and Ad35.TBS.alt ITR. These viruses were subjected to passaging in PER.C6 cells and the sequence of the 8 terminal ITR nucleotides was monitored by PCR analysis of each viral passage number. To distinguish the original from the alternative sequence, different PCR primer sets that specifically amplified either the original or the alternative ITR sequence were utilized. Analysis of each viral passage identified a decrease of the original sequence between VPN 3 and VPN6 and the emergence of the alternative sequence at VPN6 for passaging of Ad35.TBS.ori ITR (FIG. 1A). The alternative sequence was remained over 4 passages (FIG. 1A). During the passaging of artificially created Ad35.TBS.alt, only the alternative PCR sequence was detectable over 10 viral passages (FIG. 1B), excluding reversion to the original sequence or general instability within this part of the genome.

Furthermore, mixing of Ad35 vectors with alternative or original ITR sequences, which were otherwise identical, also led to outgrowth of the alternative ITR sequence, indicating a growth advantage of the alternative over the original ITR sequence.

Since we detected the switch from the original ITR sequence to an alternative ITR sequence in Ad35, a group B vector, we additionally analyzed Ad5.empty.ori ITR and Ad35.empty.alt ITR, a group C vector harboring either original or alternative ITR sequences. In contrast to the results with the Ad35 vector, Ad5 did not display a switch in the ITR sequence, but retained the original ITRs over 10 viral passages (FIG. 1C) (however, see example 8 below, showing that the alternative sequence was also found in Ad5 upon further passaging). Moreover, artificially generated Ad5 harboring alternative ITRs was stable over 10 viral passages and did not revert to the original ITR sequence (FIG. 1D).

Example 4

Ad35 Harboring the Alternative ITR Sequence Induces CPE at an Earlier Time Point Post Infection than Ad35. On ITR Since we observed outgrowth of virus genomes with alternative ITRs, we assumed that viruses with alternative ITRs should have a replication advantage over those with original ITRs for Ad35. To test this, we used Ad35 viruses harboring either original or alternative ITR sequences and analyzed their growth kinetics. Since the CPE induced by adenoviral infection on E1-complementing cell lines is a good indication for replication speed, we first infected 293 cells and looked at the cytopathic effect at 24 h, 48 h, 72 h and 96 h post infection (hpi) at an MOI of 100 VP/cell and 1000 VP/cell. At 24 h post infection, no CPE was observed for both 100 and 1000 VP/cell. However, at 48 hpi advanced CPE is observed for Ad35.dE1.alt ITRs at both 100 and 1000 VP/cell, developing into full CPE at 96 hpi. By contrast, only limited CPE was seen for Ad35.dE1.ori ITR at these time points post infection.

Example 5

The Alternative ITR Sequence Confers a Genome Replication Advantage

Figure 2:
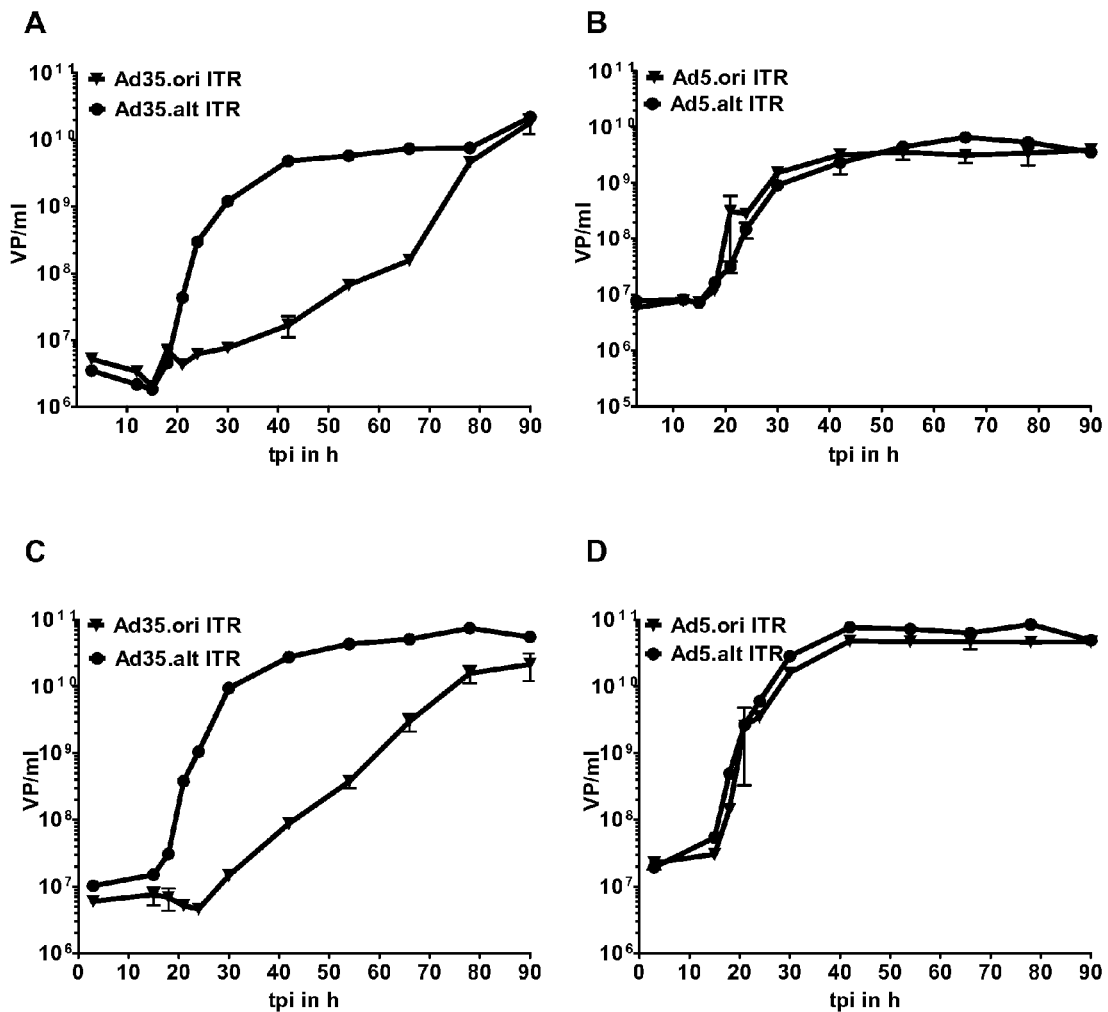
FIG. 2. Replication kinetics of Ad35 and Ad5 vectors with alternative and original ITR sequences. For details, see example 5.

To be able to quantify the suspected difference in replication kinetics, we took advantage of qPCR analysis to measure genome replication at different time points post infection. More specifically, 293 cells were infected at 1000 VP/cell, lysed and subjected to qPCR analysis using a TaqMan assay detecting the CMV promoter, present in the viral vector. As shown in FIG. 2, while both Ad35.ori ITR and Ad35.alt ITR grow to the same titer of approximately $10^{10}$ VP/ml at the latest measured time point (90 hpi) Ad35.ori ITR shows a delayed growth. At early time points post infection, Ad35.alt ITR displays a steeper genome amplification curve, reaching the plateau phase earlier than Ad35.ori ITR (FIG. 2A). In contrast, replication kinetics of Ad5, do not differ for viruses harboring alternative or original ITRs (FIG. 2B).

This genome replication advantage, that is observed for Ad35.alt ITR, but not for Ad5.alt ITR was corroborated on PER.C6 cells (FIG. 2 C-D), on which outgrowth of the alternative genome version was originally observed.

Example 6

The Alternative ITR Sequence is Represented in Published Human Adenovirus Sequences We analyzed whether the alternative ITR sequence was also present in published adenovirus sequences. Thereto, an alignment of nucleotides 1-8 of published human and nonhuman ITRs was performed. Human viruses predominantly harbor the original CATCATCA (nucleotides 1-8 of SEQ ID NO:6) sequence and were consequently categorized as "conserved human sequences" (Table I).

Additionally, sequences differing from CATCATCA (nucleotides 1-8 of SEQ ID NO:6) in one to six nucleotides were identified and termed "variable human adenovirus sequences." The predominant sequence among the "variable sequences" was the alternative sequence CTATCTAT (nucleotides 1-8 of SEQ ID NO:7) that we also identified by passaging Ad35 derived vectors. The alignment of the nonhuman sequences (Table I) shows that CATCATCA (nucleotides 1-8 of SEQ ID NO:6) is the most frequent sequence. Again, alternative sequences are found, e.g., the previously identified alternative sequence GATGATGT, which is found in fowl adenoviruses. The majority of the published ITR sequences are consistent with the replication model by de Jong (de Jong et al., 2003, *Curr Top Microbiol Immunol* 272: 187-211; King & van der Vliet, 1994, *EMBO J*. 13: 5786-5792), with a small, two, three or four nucleotide direct repeat that is required for the jumping back mechanism during replication initiation.

It is noted, that Table I shows published ITR sequences that may not be a balanced representation of naturally occurring ITR sequences. In some cases, the terminal nucleotides of the ITRs have not been sequenced but simply inferred to be CATCATCA (nucleotides 1-8 of SEQ ID NO:6). Additionally, prior to sequencing growing of adenoviruses from diagnostic swaps is common involving several replication cycles that could result in nucleotide changes. Nevertheless, it is noted that the original sequence CATCATCA (nucleotides 1-8 of SEQ ID NO:6) is still detected in nature after a long period of virus host co-evolution, and hence the alternative sequence CTATCTAT (nucleotides 1-8 of SEQ ID NO:7) may be more beneficial in cell culture than in nature.

Example 7

Repeated Passaging Leads to a Switch in ITR Sequence on a Variety of Cell Lines

To rule out that the observed switch from original to alternative ITRs is a phenomenon restricted to the production E1-complementing cell line, we passaged Ad35.wt virus containing the original ITR sequence CATCATCA (nucleotides 1-8 of SEQ ID NO:6) on a variety of cell types. Therefore, Ad35 wt was rescued using plasmids containing the complete Ad35 wild-type genome on A549, HEK293, PER.C6, Hep2, HeLa and MRC5 cells. The specific cell lines were chosen to present a broad variety of cell types, including cell lines derived from different tissues, of carcinoma and non-carcinoma origin, epithelial and fibroblastic cell lines and different ploidities (Table III).

The results in Table III show that the switch to alternative ITRs is observed at VPN 10 for the helper cell lines HEK293 and PER.C6 cells, but a switch or a mixing phenotype is also observed for the other tested cell lines, albeit at a later passage number.

Example 8

Extended Passaging Induces ITR Heterogeneity or a Complete Shift to the Alternative ITR Sequence in the Majority of the Tested Adenovirus Vectors The generality of switching to the alternative CTATCTAT (nucleotides 1-8 of SEQ ID NO:7) sequence for adenoviral vectors based upon various serotypes was investigated. Hereto, we passaged Ad26, Ad48, Ad49, Ad11(a), Ad50 and Ad5 derived adenoviral vectors on PER.C6 cells. Viral vectors were passaged until VPN 15 after plaque purification and analyzed by sequencing at VPN 10 and VPN 15. Two different transgenes were included for each vector serotype to additionally exclude an effect of a different transgene.

The results of this set of experiments are shown in Table IV. Surprisingly, we found that all tested vectors except Ad48 switch to the alternative ITR sequence or display a mixing phenotype suggesting that they would convert at a later viral passage number. In line with what we previously observed for Ad5, the original ITR sequence was remained at VPN 10, however, started to mix at VPN15. In contrast, Ad48 derived vectors were the only ones to retain the original ITR sequence up to VPN 15.

However, to stay on the safe side, we suggest to equip all recombinant adenoviruses, including the ones based on Ad5 or even Ad48, with the alternative ITR sequences hereof, in order to prevent potential batch heterogeneity due to mutations at the genome ends during culturing of large volumes or after extended passaging. This will ensure that batches of recombinant adenovirus are obtained wherein the genomes of essentially all adenovirus particles comprise the 5' terminal sequence CTATCTAT (nucleotides 1-8 of SEQ ID NO:7) hereof. Moreover, the rescuing of adenoviral vectors harboring this alternative ITR sequence may accelerate production of vaccine vectors.

TABLE I

5' terminal sequences of adenoviral serotypes

| A | Human sequences | | | B | Nonhuman sequences | | |
|---|---|---|---|---|---|---|---|
| Conserved human sequences | Human AdV 5 | L43079 | CAT CAT CA | | Simian AdV 46 | FJ025929 | CAT CAT CA |
| | Human AdV 2 | ADRCG | ... ... .. | | Simian AdV 29 | FJ025916 | ... ... .. |
| | Human AdV 1 | AF534906 | ... ... .. | C | Simian AdV 28 1 | FJ025914 | ... ... .. |
| | Human AdV 6 | FJ349096 | ... ... .. | | Simian AdV 41.1 | FJ025913 | ... ... .. |
| | Human AdV 57 | HQ003817 | ... ... .. | | Simian AdV 32 | FJ025911 | ... ... .. |
| | Human AdV 17 | HQ910407 | ... ... .. | | Simian AdV 46 | FJ025930 | ... ... .. |
| | Human AdV 19 | AB448774 | ... ... .. | | Simian AdV 27.1 | FJ025909 | ... ... .. |
| | Human AdV 22 | FJ619037 | ... ... .. | | Simian AdV 33 | FJ025908 | ... ... .. |
| | Human AdV 26 | EF 153474 | ... ... .. | | Simian AdV 35.1 | FJ025912 | ... ... .. |
| | Human AdV 28 | FJ824626 | ... ... .. | | Simian AdV 44 | FJ025899 | ... ... .. |
| | Human AdV 36 | GQ384080 | ... ... .. | | Simian AdV 31.1 | FJ025906 | ... ... .. |
| | Human AdV 36 | DQ900900 | ... ... .. | D | Simian AdV 42.1 | FJ025903 | ... ... .. |
| | Human AdV 46 | AY875648 | ... ... .. | | Simian AdV 40.1 | FJ025907 | ... ... .. |
| | Human AdV46 | EF 153473 | ... ... .. | | Simian AdV 34 | FJ025905 | ... ... .. |
| | Human AdV 49 | DQ393829 | ... ... .. | | Simian AdV 45 | FJ025901 | ... ... .. |
| | Human AdV 53 | AB605244 | ... ... .. | | Simian AdV 43 | FJ025900 | ... ... .. |
| | Human AdV 54 | AB448770 | ... ... .. | | Simian AdV 50 | HQ241820 | ... ... .. |
| | Human AdV 56 | HM770721 | ... ... .. | | Simian AdV 49 | HQ241819 | ... ... .. |
| | Human AdV 3 | AY599836 | ... ... .. | | Simian AdV SA7P | X01027 | ... ... .. |
| | Human AdV 7 | AY601634 | ... ... .. | | Simian AdV 8 | ADRITR1 | ... ... .. |
| | Human AdV 11a | FJ597732 | ... ... .. | | Simian AdV 7 | DQ792570 | ... ... .. |
| | Human AdV 14 | AY803294 | ... ... .. | B | Simian AdV 1 | AY771780 | ... ... .. |
| | Human AdV 34 | AY737797 | ... ... .. | | Simian AdV 30 | FJ025920 | ... ... .. |
| | Human AdV 35 | AY128640 | ... ... .. | | Simian AdV 23 | AY530877 | ... ... .. |
| | Human AdV 55 | FJ643676 | ... ... .. | | Simian AdV 39 | FJ025924 | ... ... .. |
| | Human AdV 4 | AY599837 | ... ... .. | E | Simian AdV 22 | AY530876 | ... ... .. |
| | Human AdV 40 | L19443 | ... ... .. | | Simian AdV 36 | FJ025917 | ... ... .. |
| | Human AdV 41 | OQ315364 | ... ... .. | F | Simian AdV 26 | FJ025923 | ... ... .. |
| | Human AdV 31 | AM748299 | ... ... .. | | Simian AdV 37 2 | FJ025919 | ... ... .. |
| | Human AdV 18 | ADRP1IT1 | ... ... .. | A | Simian AdV 24 | AY530878 | ... ... .. |
| | | | | | Simian AdV 36 | FJ025917 | ... ... .. |
| Variable human sequences | Human AdV 10 | ADRJITR-1 | .T. ... .. | | Simian AdV 25 | FJ025918.1 | ... ... .. |
| | Human AdV 19 | ADRITRAA | ..A T.A T. | | Simian AdV 25 | AF394198 | .C. TC. TC |
| | Human AdV 6 | AB448769 | .TA TC. AT | | Simian AdV 21 | AC000010 | .CA TCA TC |
| | Human AdV 29 | AB562587 | .TA TC. AT | D | Equine AdV 1 | AEEADITR1 | ... ... .. |
| | Human AdV 53 | AB605246 | .TA TC. AT | | Porcine AdV 3 | AF083132 | ... ... .. |
| | Human AdV 15 | AB562586 | .TA TC. AT | | Porcine AdV 5 | AF221544-1 | ... ... .. |
| | Human AdV 37 | AF271992 | .TA TC. AT | | Bovine AdV 2 | AF252854-1 | ... ... .. |
| | Human AdV 9 | AF099665 | .TA TC. AT | | Bovine AdV 1 | ADRITRB | ... ... .. |
| | Human AdV 3 | DQ086466 | .TA TC. AT | | Bovine AdV 3 | AF030154 | ... ... .. |
| | Human AdV 7 | HQ659699 | .TA TC. AT | | Bovine AdV 4 | AF036092 | ... TCA T. |
| | Human AdV 7 | AY495969 | .TC TC. AT | B | Bovine AdV 5 | AF238881 | ... TCA T. |
| | Human AdV 16 | AY601636 | ... T.. .T | | Bovine AdV 10 | AF238882 | ... ... .. |
| | Human AdV 21 | AY601633 | .TA TC. AT | | Canine AdV 2 | CAU77082 | ... ... .. |
| | Human AdV 50 | AY737798 | ..A TCA AT | | Canine AdV 1 | AC_000003 | ... ... .. |
| | Human AdV 4 | AY458656 | .TC TC. .T | | Murine AdV 1 | ADRITRRA | ... ... .. |
| | Human AdV 4 | AY594253 | .TA TC. AT | E | Murine AdV 3 | EU835513 | ... ... .. |
| | Human AdV 41 | HM565136 | G.G TG. TG | F | Murine AdV 2 | NC_014899 | .T. .T. ... |
| | Human AdV 18 | GU191019 | .C. ATC T. | | Tree Shrew AdV 1 | AF258784 | ... ... .. |
| | Human AdV 12 | AC_000005 | .C. ATC T. | A | Mast AdV | ADRFRG | G.. G.. GT |
| | Consensus | | CAT CAT CA | | Ovine AdV 7 | OAU40839 | .TA TTC AT |

Mast-AdV

TABLE I-continued

| | | | |
|---|---|---|---|
| Turkey AdV A | AC_000016 | ..A TCA AT | ⎫ |
| Turkey AdV A | AC_000016-1 | ..A TCA AT | ⎬ Si-AdV |
| Turkey AdV 1 | NC_014564 | ... ... .T | |
| Frog AdV 1 | NC_002501 | ..A TCA AT | ⎭ |
| Fowl AdV 1 | AAU46933 | G.. G.. GT | ⎫ |
| Fowl AdV 1 | AY421750S1 | ... ... .T | |
| Fowl AdV 1 | AY421750S2 | ... A.C .G | ⎬ Avi-AdV |
| Fowl AdV C | NC_015323 | ... ... .T | |
| Fowl AdV 9 | AF083975 | ... ... .T | |
| Fowl AdV E | NC_014959 | ... ... .T | ⎭ |
| Duck AdV A | AC_000004 | .TC ATG TC | } At-AdV |
| | Consensus | CAT CAT CA | |

TABLE II

ITRs of various rAd35 viruses upon passaging

| Virus | pIX promoter | Genome size (kbp) | # PP | ITR |
|---|---|---|---|---|
| Ad35.TBS | + | 32.4 | 2 | Mixing |
| Ad35.Ebo.GP.Z | + | 32.4 | 2 | alternative |
| Ad35.Ebo.GP.S/G | + | 32.4 | 2 | Mixed |
| Ad35.CS | + | 31.5 | 1 | Mixed |
| Ad35.CS | − | 31.3 | 1 | original |
| Ad35.Luc | + | 32.0 | 1 | Mixing |
| Ad35.Luc | − | 31.9 | 1 | Mixed |
| Ad35.eGFP | + | 31.1 | 1 | Mixing |
| Ad35.eGFP | − | 30.9 | 1 | Mixed |
| Ad35.Empty | + | 30.4 | 1 | alternative |
| Ad35.Empty | − | 30.2 | 1 | alternative |
| Ad35.SIV-Gag | + | 31.9 | 1 | alternative |
| Ad35 wild type | NA | 34.8 | 1 | Mixed |

TABLE III

ITR switch on different cell lines

| Ad35wt | Cell type | origin | ploidy | VP10 | VP15 |
|---|---|---|---|---|---|
| HEK293 | Helper E1, kidney | epithelial | diploid | alternative | — |
| PER.C6 | Helper E1, retina | epithelial | hypotriploid | alternative | — |
| A549 | Lung carcinoma | epithelial | hypotriploid | mixing | Mixing |
| HeLa | Cervix adeno-carcinoma | epithelial | hypotriploid | — | alternative |
| Hep2 | HeLa contaminant | epithelial | diploid | original | Mixing |
| MRC5 | Normal lung | fibroblast | diploid | — | mixing |

TABLE IV

ITR switch of different vectors

| Vector | Subgroup | VPN 10 | VPN 15 |
|---|---|---|---|
| Ad26.eGFP | D | mixed | Alternative |
| Ad26.Luc | D | mixed | Alternative |
| Ad48.eGFP | D | original | Original |
| Ad48.Luc | D | original | Original |
| Ad49.eGFP | D | alternative | Nd |
| Ad49.Luc | D | mixed | alternative |
| Ad11.Env | B | alternative | Nd |
| Ad11.SivGag | B | alternative | Nd |
| Ad50.eGFP | B | alternative | Nd |
| Ad50.Luc | B | mixed | alternative |
| Ad5.eGFP | C | original | Mixing |
| Ad5.Luc | C | original | Mixing |

What is claimed is:

1. A composition comprising adenovirus particles, wherein the adenovirus is a recombinant human adenovirus of serotype 5, 11a, 26, 34, 35, 48, 49 or 50, or a recombinant simian adenovirus, wherein the genomes of essentially all adenovirus particles in the composition have as the 5' terminal nucleotides the polynucleotide: CTATCTAT, and wherein the adenovirus comprises a transgene.

2. The composition of claim 1, wherein the adenovirus is a human adenovirus of serotype 5, 26, 35, 49, or 50.

3. The composition of claim 2, wherein the adenovirus is a human adenovirus of serotype 26 or 35.

4. The composition of claim 1, which is a pharmaceutical composition.

5. The composition of claim 1, wherein the adenovirus lacks at least a portion of the E1 region.

6. The composition of claim 1, comprising at least $1\times10^7$ recombinant adenovirus particles.

7. A method for preparing a batch of recombinant adenovirus particles that have essentially all identical polynucleotides in the 5' termini of their genomes, the method comprising:
  a) performing a molecular cloning step to exchange naturally occurring 5' termini of an adenovirus genome with altered 5' termini comprising as terminal nucleotides the polynucleotide: CTATCTAT,
  b) propagating in host cells the recombinant adenovirus having the altered 5' termini, and
  c) harvesting the recombinant adenovirus to obtain a batch of recombinant adenovirus particles that essentially all have as the 5' terminal nucleotides of their genomes the polynucleotide: CTATCTAT, and wherein the adenovirus comprises a transgene.

8. A method for preparing a batch of recombinant adenovirus particles that have essentially all identical polynucleotides in the 5' termini of their genomes, the method comprising:
  a) performing a plaque purification of an adenovirus, wherein the recombinant adenovirus is a recombinant human adenovirus of serotype 5, 11a, 26, 34, 35, 48, 49 or 50, or a recombinant simian adenovirus, to isolate an adenovirus or recombinant adenovirus from a single plaque, wherein the adenovirus or recombinant adenovirus has as the 5' terminal nucleotides of its genome polynucleotide: CTATCTAT,
  b) propagating in host cells a recombinant adenovirus obtained from the single plaque of step a), and
  c) harvesting the recombinant adenovirus to obtain a batch of recombinant adenovirus particles that essentially all have as the 5' terminal nucleotides of their genomes the polynucleotide: CTATCTAT, and wherein the adenovirus comprises a transgene.

9. The method according to claim 7, wherein the batch comprises at least $1\times10^7$ recombinant adenovirus particles.

10. The method according to claim 7, wherein the recombinant adenovirus is a recombinant human adenovirus of serotype 5, 26, 35, 49, or 50.

11. The method according to claim 7, wherein the recombinant adenovirus is a recombinant human adenovirus of serotype 26 or 35.

12. The method according to claim 7, wherein the recombinant adenovirus lacks at least a portion of the E1 region.

13. The method according to claim 7, further comprising purifying the recombinant adenovirus.

14. The method according to claim 13, further comprising formulating the recombinant adenovirus into a pharmaceutical composition.

15. The method according to claim 7, wherein step b) is performed in a bioreactor.

16. The composition of claim 6, comprising at least $1\times10^8$ recombinant adenovirus particles.

17. The composition of claim 16, comprising at least $1\times10^9$ recombinant adenovirus particles.

18. The composition of claim 17, comprising at least $1\times10^{10}$ recombinant adenovirus particles.

19. The composition of claim 1, wherein the adenovirus is a human adenovirus of serotype 35.

20. The composition of claim 1, wherein the adenovirus is a human adenovirus of serotype 26.

21. The composition of claim 2, which is a pharmaceutical composition.

22. The composition of claim 3, which is a pharmaceutical composition.

23. The composition of claim 19, which is a pharmaceutical composition.

24. The composition of claim 20, which is a pharmaceutical composition.

25. The composition of claim 2, wherein the adenovirus lacks at least a portion of the E1 region.

26. The composition of claim 3, wherein the adenovirus lacks at least a portion of the E1 region.

27. The composition of claim 19, wherein the adenovirus lacks at least a portion of the E1 region.

28. The composition of claim 20, wherein the adenovirus lacks at least a portion of the E1 region.

29. The composition of claim 23, wherein the adenovirus lacks at least a portion of the E1 region.

30. The composition of claim 24, wherein the adenovirus lacks at least a portion of the E1 region.

31. The composition of claim 2, comprising at least $1\times10^{10}$ recombinant adenovirus particles.

32. The composition of claim 3, comprising at least $1\times10^{10}$ recombinant adenovirus particles.

33. The composition of claim 4, comprising at least $1\times10^{10}$ recombinant adenovirus particles.

34. The composition of claim 5, comprising at least $1\times10^{10}$ recombinant adenovirus particles.

35. The composition of claim 19, comprising at least $1\times10^{10}$ recombinant adenovirus particles.

36. The composition of claim 20, comprising at least $1\times10^{10}$ recombinant adenovirus particles.

37. The composition of claim 21, comprising at least $1\times10^{10}$ recombinant adenovirus particles.

38. The composition of claim 22, comprising at least $1\times10^{10}$ recombinant adenovirus particles.

39. The composition of claim 23, comprising at least $1\times10^{10}$ recombinant adenovirus particles.

40. The composition of claim 24, comprising at least $1\times10^{10}$ recombinant adenovirus particles.

41. The composition of claim 25, comprising at least $1\times10^{10}$ recombinant adenovirus particles.

42. The composition of claim 26, comprising at least $1\times10^{10}$ recombinant adenovirus particles.

43. The composition of claim 27, comprising at least $1\times10^{10}$ recombinant adenovirus particles.

44. The composition of claim 28, comprising at least $1\times10^{10}$ recombinant adenovirus particles.

45. The composition of claim 29, comprising at least $1\times10^{10}$ recombinant adenovirus particles.

46. The composition of claim 30, comprising at least $1\times10^{10}$ recombinant adenovirus particles.

* * * * *

SEQUENCE LISTING

```
<160> NUMBER OF SEQ ID NOS: 14

<210> SEQ ID NO 1
<211> LENGTH: 17
<212> TYPE: DNA
<213> ORGANISM: Artificial
<220> FEATURE:
<223> OTHER INFORMATION: primer

<400> SEQUENCE: 1
gtgactggtg agtactc                                                     17

<210> SEQ ID NO 2
<211> LENGTH: 16
<212> TYPE: DNA
<213> ORGANISM: Artificial
```

```
<220> FEATURE:
<223> OTHER INFORMATION: primer

<400> SEQUENCE: 2
gaccacctag gctgac                                                    16

<210> SEQ ID NO 3
<211> LENGTH: 37
<212> TYPE: DNA
<213> ORGANISM: Artificial
<220> FEATURE:
<223> OTHER INFORMATION: primer

<400> SEQUENCE: 3
ttaattaatc gatctatcta tataatatac cttatag                             37

<210> SEQ ID NO 4
<211> LENGTH: 36
<212> TYPE: DNA
<213> ORGANISM: Artificial
<220> FEATURE:
<223> OTHER INFORMATION: primer

<400> SEQUENCE: 4
gatctatcta tataatatac cttatagatg gaatgg                              36

<210> SEQ ID NO 5
<211> LENGTH: 35
<212> TYPE: DNA
<213> ORGANISM: Artificial
<220> FEATURE:
<223> OTHER INFORMATION: primer

<400> SEQUENCE: 5
attatataga tagatcgatt aattaattcg aaccc                               35

<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
catcatcaat aatatacc                                                  18

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
ctatctatat aaatatacc                                                 18

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
ctaagtagtt ccgtgagaaa ag                                             22
```

```
<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
ggtacgtcac atcccattaa                                               20

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
cacttttgcc acatccgtc                                                19

<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11
cccacgttac gtcacttc                                                 18

<210> SEQ ID NO 12
<211> LENGTH: 17
<212> TYPE: DNA
<213> ORGANISM: Artificial
<220> FEATURE:
<223> OTHER INFORMATION: primer

<400> SEQUENCE: 12
tgggcggtag gcgtgta                                                  17

<210> SEQ ID NO 13
<211> LENGTH: 22
<212> TYPE: DNA
<213> ORGANISM: Artificial
<220> FEATURE:
<223> OTHER INFORMATION: primer

<400> SEQUENCE: 13
cgatctgacg gttcactaaa cg                                            22

<210> SEQ ID NO 14
<211> LENGTH: 18
<212> TYPE: DNA
<213> ORGANISM: Artificial
<220> FEATURE:
<223> OTHER INFORMATION: primer

<400> SEQUENCE: 14
tgggaggtct atataagc                                                 18
```